(12) United States Patent
Fabregat et al.

(10) Patent No.: US 8,305,423 B2
(45) Date of Patent: Nov. 6, 2012

(54) COMMUNICATION SYSTEM FOR REMOTE PATIENT VISITS AND CLINICAL STATUS MONITORING

(75) Inventors: M. Elena Fabregat, Alicante (ES); Francisco Ibanez Garcia, Vilena (ES); Pedro Mateo Riobo Aboy, Beaverton, OR (US)

(73) Assignee: Innovatec, S.L., Alcoi (ES)

( * ) Notice: Subject to any disclaimer, the term of this patent is extended or adjusted under 35 U.S.C. 154(b) by 422 days.

(21) Appl. No.: 12/625,529

(22) Filed: Nov. 24, 2009

(65) Prior Publication Data

US 2010/0128104 A1  May 27, 2010

Related U.S. Application Data

(60) Provisional application No. 61/117,240, filed on Nov. 24, 2008.

(51) Int. Cl.
*H04N 7/14* (2006.01)
(52) U.S. Cl. .......... 348/14.08; 348/14.03; 348/14.09
(58) Field of Classification Search ............ 348/14.01, 348/14.03, 14.08, 14.12; 705/2
See application file for complete search history.

(56) References Cited

U.S. PATENT DOCUMENTS

| | | | |
|---|---|---|---|
| 7,197,467 B2 | 3/2007 | Labadie | |
| 7,965,309 B2* | 6/2011 | Mattila et al. | 348/14.08 |
| 2006/0064324 A1 | 3/2006 | Rosenfeld et al. | |
| 2006/0087555 A1* | 4/2006 | Boyd et al. | 348/14.09 |
| 2007/0285504 A1* | 12/2007 | Hesse | 348/14.08 |
| 2008/0201158 A1* | 8/2008 | Johnson et al. | 705/1 |
| 2009/0240521 A1* | 9/2009 | Simons et al. | 705/2 |

* cited by examiner

*Primary Examiner* — Quoc D Tran
(74) *Attorney, Agent, or Firm* — Mateo Aboy; Aboy & Associates PC

(57) ABSTRACT

Disclosed embodiments include a telemedicine communication system designed to make possible "virtual" patient visits by approved visitors such as the spouse, family, and friends of the hospitalized patient having the appropriate digital certificate and visitation/communication permissions. According to one embodiment, the system enables relatives to visit hospitalized patients using audiovisual communication modalities selected according to the severity and health status of the patient. Additionally, the system provides functionality to enable approved relatives to follow the health status of the patient according to their permissions.

7 Claims, 3 Drawing Sheets

COMMUNICATION SYSTEM FOR REMOTE PATIENT VISITS AND CLINICAL STATUS MONITORING

CROSS-REFERENCE TO RELATED APPLICATIONS

This application claims the benefit of U.S. Provisional Application No. 61/117,240 filed on Nov. 24, 2008 by the present inventors, which is incorporated herein by reference.

BACKGROUND

1. Field of Invention

This invention relates to medical systems. Specifically, it relates to telemedicine systems.

2. Related Art

Telemedicine systems are well known. Several telemedicine systems have been proposed in research journals and patents. These systems are primarily designed to solve the problem of remote medical assistance. For instance, various systems have been designed to provide home-based remote medical assistance, home monitoring, and to involve remote medical experts for the purposes of providing care. However, none of the systems found in related art has been designed specifically to facilitate communication between the clinical provider, patients, and their families wishing to "visit" them while at remote locations. A system that makes possible rich life-like audiovisual communication between patients and their virtual visitors has a lot of potential to improve the quality of life for patients, families, and friends.

SUMMARY

The remote medical visitation system comprises: (a) a plurality of client access points for patients, relatives (virtual visitors), and clinicians; and these client access points comprise one or more audio-visual systems connected by a network upon completion of a secure authentication procedure; (b) a secure computer server running an integrated web-enabled platform supporting encrypted data transfer including a relational database to store user profiles, visitation protocols, user data, videoconferencing schedules, and communication information from a plurality of patients, relatives, and clinicians; and (c) a plurality of software modules including a plurality of graphical user interfaces for control, planing, communication activation, and report creation. According to a particular embodiment, the software modules include a module to manage and program a communication protocol between patients and their virtual visitors depending on a patient's health status.

BRIEF DESCRIPTION OF THE DRAWINGS

Disclosed embodiments are illustrated by way of example, and not by way of limitation, in the figures of the accompanying drawings.

DETAILED DESCRIPTION

Figure 1:
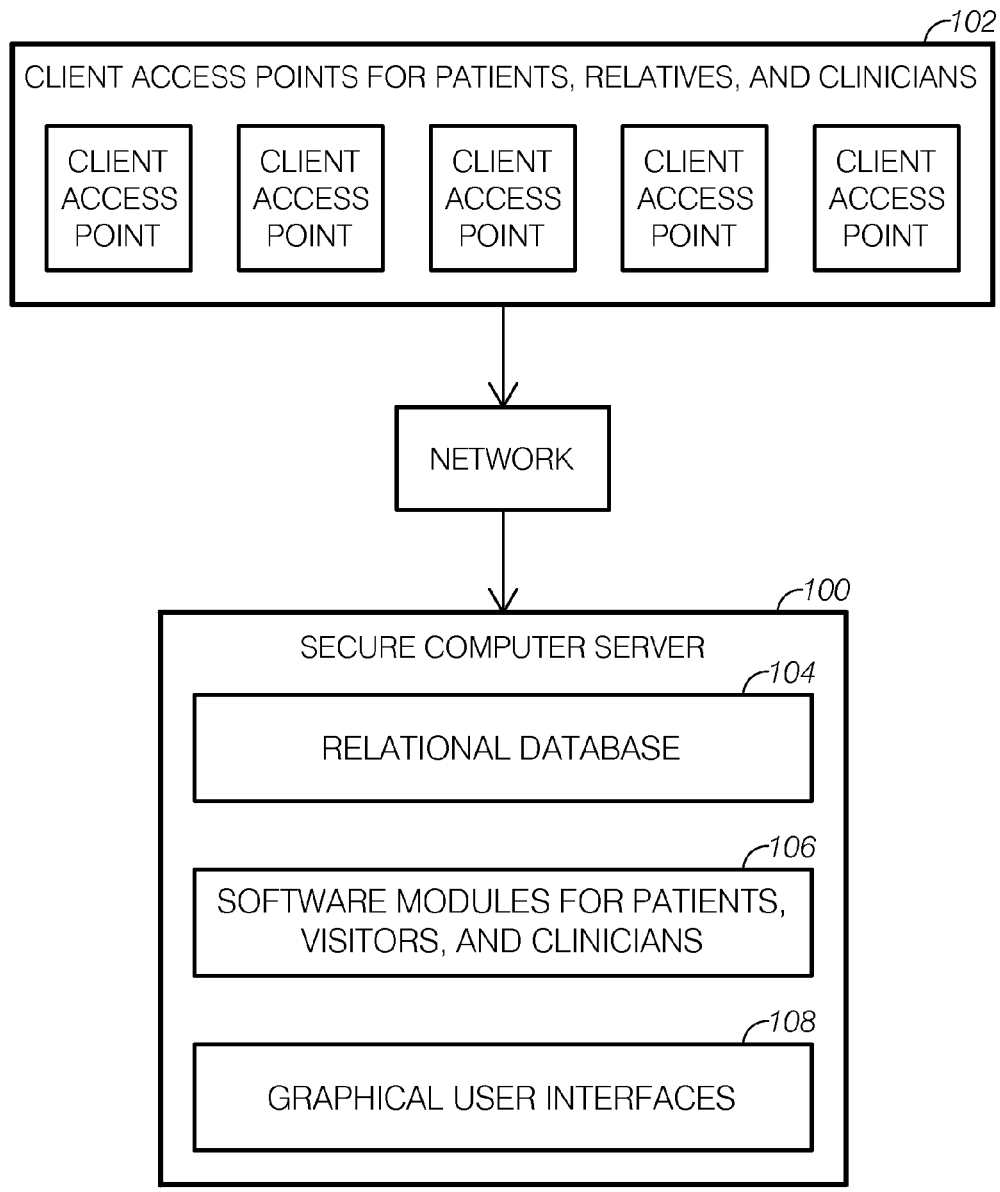
FIG. 1 illustrates a block diagram representing the main modules of the remote visitation system according to one embodiment.

As shown in FIG. 1, according to one embodiment the remote medical visitation system comprises: (a) a plurality of client access points for patients, relatives (virtual visitors), and clinicians 102; and these client access points comprise one or more audio-visual systems connected by a network upon completion of a secure authentication procedure; (b) a secure computer server 100 running an integrated web-enabled platform supporting encrypted data transfer including a relational database 104 to store user profiles, visitation protocols, user data, videoconferencing schedules, and communication information from a plurality of patients, relatives, and clinicians; and (c) a plurality of software modules 106 including a plurality of graphical user interfaces 108 for control, planing, communication activation, and report creation. According to a particular embodiment, the software modules include a module to manage and program a communication protocol between patients and their virtual visitors depending on a patient's health status.

In one embodiment the system comprises a computer server that runs an integrated web-enabled platform designed for audio-visual web communication and a plurality of clients equipped with networked audio-visual systems. It supports encrypted data transfer through standard encryption protocols. A relational database such as MySQL is used to store user profiles, protocols, user data, videoconferencing schedules, and communication information from patients, doctors, and relatives. The multi-platform system is built to include security, backups, and redundancy. All users are authenticated and the data is carefully controlled to ensure compliance with federal regulatory requirements such as the Health Information Portability and Accountability Act (HIPAA).

According to one embodiment, the system includes modules for control, planning, communication activation, and report creation for the health-care providers. The system includes a comprehensive digital health information management module, and a communication plan for direct communication with family members according to their permissions through web, SMS, email, and substantially equivalent technologies.

According to one embodiment, the system includes a module to manage and program the communication protocol between patients and their virtual visitors depending on their health status (e.g. full video conference, partial image video conference, image only, video off, etc). Additionally, the system provides the capability for the health professionals in charge of patient care to monitor the virtual visits in order to avoid visitations during real-time health complications and other inappropriate times.

According to one embodiment, the system includes a client application for approved visitors that upon installation enables for secure communications with the health professionals and patient according to a pre-programmed visitation protocol established by the hospital.

According to one particular embodiment, and without limitation, the server accepts video conference petitions and makes them possible using asterisk and MeetMe/Confiance plug-ins. The system reports use a local MySQL database that is only accessible by the server. The communication between the client and the server is implemented using RMI technology programmed in JAVA or a substantially equivalent language. The server publishes the methods that each user can access and access the secure local database as required. The video conference system employs the SIP protocol over a PBX voice over IP central, Asterisk. Using the MeetMe and Confiance plug-ins the system is capable of establishing video conferences from the software client or any other device with VoIP capabilities. Furthermore, Asterisk enables for establishing pathways to the basic phone network and mobile networks.

The following descriptions explain how each type of user may use the communication platform; the system includes modules to accommodate each of these uses. In one embodiment, a clinical module is especially adapted to enable clinicians to: 1) manage the system users (patients, relatives, friends) and enable the use of the virtual visitation system during the hospitalization period; 2) generate reports of the clinical status, action plans, external communications with approved family members with access to such information and automatic transmission of these reports by SMS or email; 3) have access to the history of reports, communication to family and management of these; 4) program the virtual visitations sessions including dates, times, multimedia options (video, audio, text) and manage them according to the patient recovery; 5) perform real-time monitoring of active visits in order to provide clinical supervision when needed; and 6) access to the patient webcam in order to capture images and video to be sent to family members in situations where real-time full video conference visitations are not allowed due to patient condition or other reasons.

According to one embodiment, the communication system includes a relatives and friends module especially adapted to enable relatives (family visitors, friends, etc) to: 1) access the system upon downloading and installing the client application upon secured identification using a digital certificate as approved visitors with corresponding permissions; 2) access historical health reports generated by the health providers or general health status depending on the level of permissions; 3) access the visitation calendar (dates, times) programmed by the clinical staff according to the visitation schedule and patient condition; 4) video conference access in real-time during scheduled times according to the modality selected by the clinical staff (i.e. full video/audio, partial video/audio, audio, text); and 5) access to said multi-media material such as photographs, pre-recorded video and upload multimedia materials (pictures, videos, audio, etc) for the patient to the multimedia space. The patients module is especially adapted to enable patients with different conditions to access the video conference and communication system and communicate with family, relatives, and friends.

Figure 2:
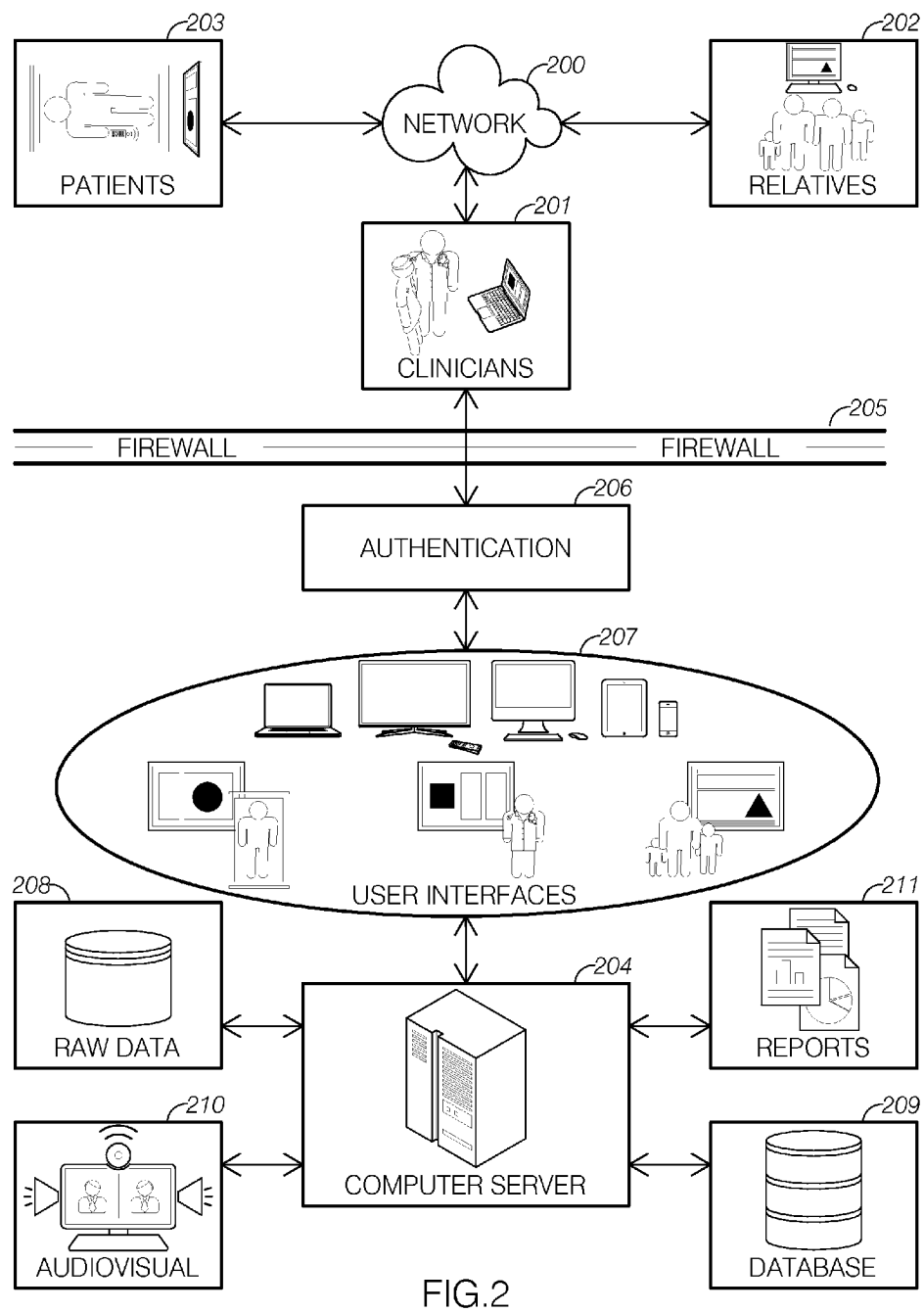
FIG. 2 illustrates an example of a system architecture according to one embodiment.

FIG. 2 illustrates an example of the system architecture according to one embodiment. In this embodiment, the clinicians' client access point 201, the relatives' client access point 202, and the patients' client access point 203 are connected to a communication network 200 with access to a central server 204 through a secure firewall 205. Each user goes through a user-specific authentication procedure 206 and has a user-specific interface 207. According to this embodiment the system components comprise a central server 204, a database to store raw data 208, a user database 209, an audio/video conferencing system 210, and an automatic reports generator engine 211.

Figure 3:
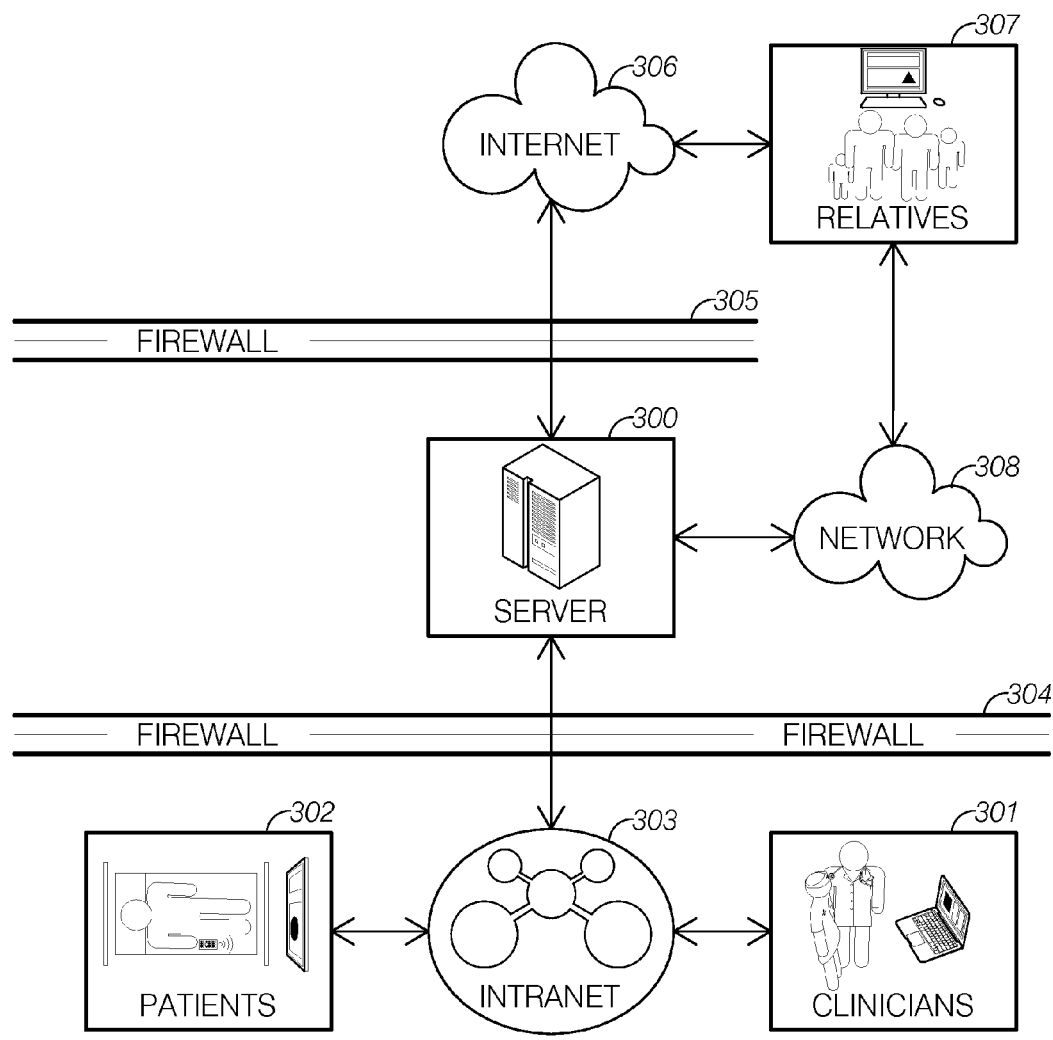
FIG. 3 illustrates a block diagram representing the access modalities to the system according to the user profile.

FIG. 3 illustrates an example of a access to the system according to one embodiment. In this embodiment, a particular clinicians' client access point 301 and patients' client access point connect to the server 300 and the system components described in FIG. 2, through a secure firewall 304 using a Intranet network 303. The relatives client access point 307 connects to the server 300 and the system components described in FIG. 2 through a secure firewall 305 using the Internet 306 and the EDGE, GSM, 3G, 4G, WIMAX or substantially equivalent networks 308. According to one embodiment the system automatically sends clinical reports by SMS and substantially equivalent technologies to the mobile phone of the approved relatives. Each client access point comprises a hardware system with one or more processors, audio capability (e.g. microphone), an optional video monitoring system (e.g. a video camera), and network connectivity.

According to one embodiment the proposed system is designed to comply with protocols used by the military in order to allow family members to visit and support hospitalized soldiers during their recovery period. According to a particular embodiment the secure computer server includes secure communications protocols especially adapted to comply with military security standards including protocols substantially equivalent to the Secure Communications Interoperability Protocol (SCIP). Other embodiments include additional secure communications protocols such as FNDT, STU-III, and STE.

While particular embodiments and example results have been described, it is understood that, after learning the teachings contained in this disclosure, modifications and generalizations will be apparent to those skilled in the art without departing from the spirit of the disclosed embodiments.

The invention claimed is:

1. A remote medical visitation system, comprising:
   (a) a plurality of client access points for patients, relatives, and clinicians; said client access points comprising one or more audio-visual systems connected by a network upon completion of a secure authentication procedure;
   (b) a secure computer server running an integrated web-enabled platform supporting encrypted data transfer including a relational database to store user profiles, visitation protocols, user data, videoconferencing schedules, and communication information from a plurality of patients, relatives, and clinicians; and
   (c) a plurality of software modules including a plurality of graphical user interfaces for control, planing, communication activation, and report creation, wherein said plurality of software modules include a module to manage and program a communication protocol between patients and their virtual visitors depending on a patient's health status, and wherein said module to manage and program a communication protocol automatically selects a communication modality as a function of the patient's health status, said communication modality is chosen from the group consisting of full video conference, partial image video conference, static image audio conference, audio conference, and text conference.

2. The remote medical visitation system of claim 1, wherein said audio-visual systems comprise a plurality of network enabled systems including hardware to support data, audio, and video communications.

3. The remote medical visitation system of claim 1, wherein said plurality of access points include a client application for approved visitors that upon installation enables for secure communications with said clinicians and said patients according to a pre-programmed visitation protocol determined based on the patient's health status and one or more hospital visitation regulations.

4. The remote medical visitation system of claim 3, wherein said plurality of software modules include a clinical module especially adapted to enable clinicians to 1) manage a plurality of system users (patients, relatives, friends) and enable the use of said remote medical visitation system during the hospitalization period, 2) generate a plurality of reports of the patient's health status, action plans, and external communications with approved family members with access to such information, and automatic transmission of these reports by SMS and email, 3) have access to a history of said reports, communications to relatives and management of said reports and communications; 4) program virtual visitations sessions as a visitation calendar including dates, times, multimedia options and modality (video, audio, text) and manage them according to a patient recovery status, 5) perform real-time monitoring of active visits in order to provide clinical supervision when needed; and 6) access to a patient's video camera in order to create a multimedia repository by capturing images and video to be sent to said relatives in situations where real-time full video conference visitations are not allowed due to the patient's health status.

5. The remote medical visitation system of claim 4, wherein said plurality of software modules include a virtual visitor module especially adapted to enable relatives and friends to 1) access said remote medical visitation system upon downloading and installing the client application upon secure identification using a digital certificate as approved visitors with corresponding permissions, 2) access said plurality of reports detailing the patient's health status depending on the level of permissions, 3) access said visitation calendar programmed according to a visitation schedule and the patient's health status, 4) gain video conference access in real-time during scheduled times according to the modality determined on the remote medical visitation system, and 5) access said multimedia repository to view and download contents of said repository including photographs, pre-recorded video, and audio; and upload a plurality of multimedia files to said multimedia repository for the patient.

6. The remote medical visitation system of claim 5, wherein said secure computer server includes secure communications protocols especially adapted to comply with military security standards including protocols substantially equivalent to a secure communications interoperability protocol (SCIP).

7. The remote medical visitation system of claim 6, wherein said secure computer server accepts video conference petitions and makes them possible using Asterisk and MeetMe/Confiance plug-ins, communication between the clients and the server is implemented using RMI technology, and said audio-visual conference the systems employ a SIP protocol over a PBX voice over IP central Asterisk.

* * * * *